Figure 1:
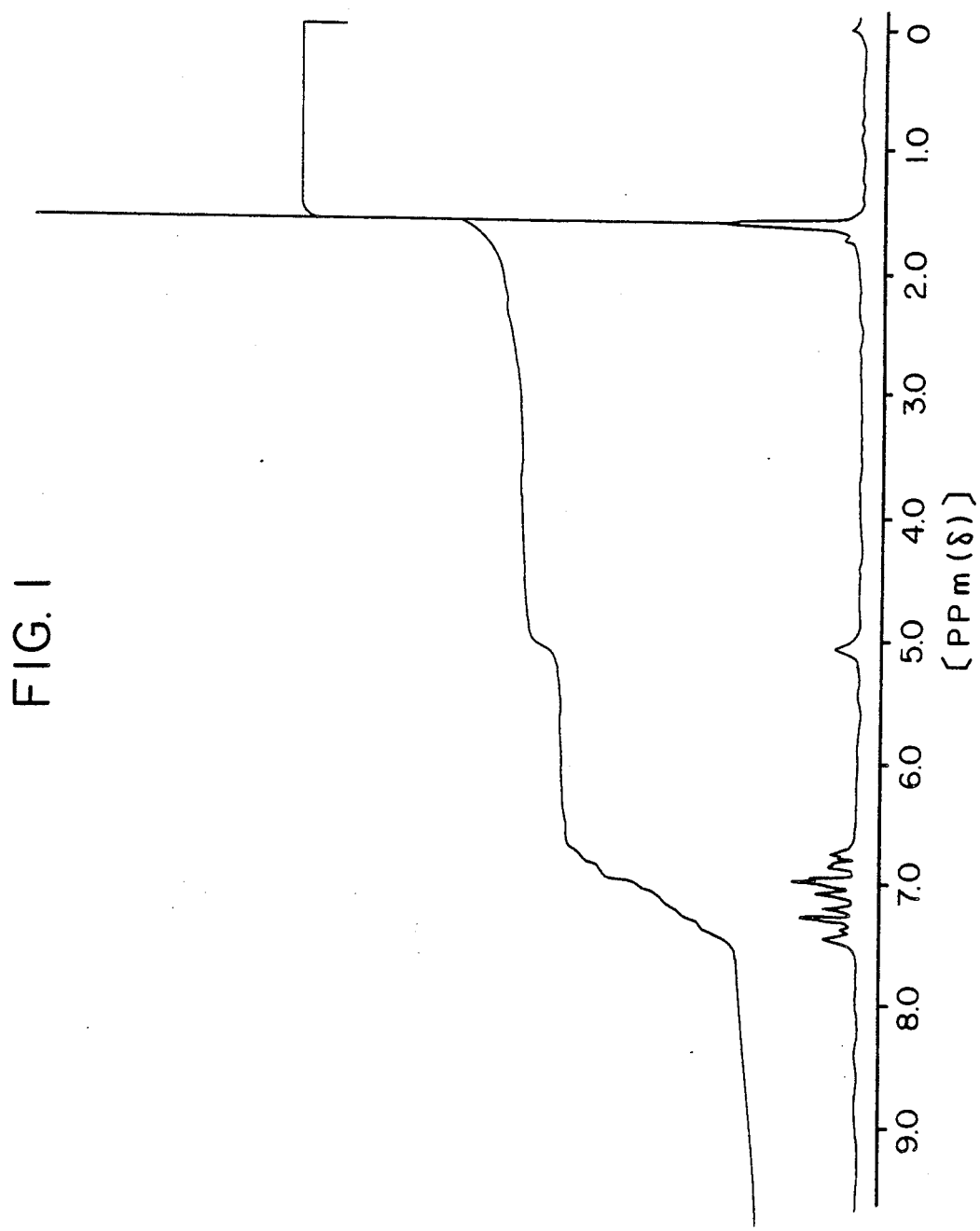

United States Patent [19]

Yorozu et al.

[11] Patent Number: 5,068,455
[45] Date of Patent: Nov. 26, 1991

[54] 3-(2-HYDROPEROXY-2-PROPYL)PHENOL AND METHOD OF PRODUCING RESORCINOL USING THE SAME

[75] Inventors: Kiyotaka Yorozu, Wakicho; Hiroyasu Ohno, Hiroshima, both of Japan

[73] Assignee: Mitsui Petrochemical Industries, Ltd., Tokyo, Japan

[21] Appl. No.: 578,206

[22] Filed: Sep. 6, 1990

Related U.S. Application Data

[62] Division of Ser. No. 305,185, Feb. 2, 1989.

[30] Foreign Application Priority Data

Feb. 4, 1988 [JP] Japan ............................ 63-025441
Nov. 15, 1988 [JP] Japan ............................ 63-288287

[51] Int. Cl.$^5$ .................... C07C 407/00; C07C 409/08
[52] U.S. Cl. ................................ 568/567; 568/568

[58] Field of Search ............. 568/568, 754, 768, 771, 568/578, 567

[56] References Cited

FOREIGN PATENT DOCUMENTS 0327361 8/1989 European Pat. Off. ............ 568/567
37741 4/1975 Japan ................................ 568/568
3309838 12/1989 Japan ................................ 568/568

*Primary Examiner*—Werren B. Lone
*Attorney, Agent, or Firm*—Sherman and Shalloway

[57] ABSTRACT

There is provided a novel organic hydroperoxide, 3-(2-hydroperoxy-2-propyl)phenol. The hydroperoxide is produced by oxidizing 3-(2-hydroxy-2-propyl)phenol or m-isopropenylphenol with hydrogen peroxide in the presence of an acid catalyst.

There is further provided a method of producing resorcinol which comprises decomposing the 3-(2-hydroperoxy-2-propyl)phenol in the presence of an acid catalyst.

4 Claims, 3 Drawing Sheets

3-(2-HYDROPEROXY-2-PROPYL)PHENOL AND METHOD OF PRODUCING RESORCINOL USING THE SAME

This is a division of application Ser. No. 07/305,185, filed Feb. 2, 1989.

This invention relates to 3-(2-hydroperoxy-2-propyl)phenol, a novel organic hydroperoxide, a method of producing the same, and a method of producing resorcinol using the same as a starting material.

Resorcinol is useful as an intermediate for production of pharmaceuticals, agricultural chemicals, resins, and many other chemicals. The compound has been heretofore produced by fusing 1,3-benzenedisulfonic acid with caustic soda, or by air-oxidizing m-diisopropylbenzene and then acid-decomposing the air-oxidized products.

However, the former method has a disadvantage in that it uses a large amount of water in the reaction, hence the process is attended by the production of a large amount of waste water, and the treatment of the waste water costs a great deal. The latter method needs very severe reaction conditions to oxidize and acid-decompose the two propyl groups of m-diisopropylbenzene at the same time, so that a large amount of undesired by-products are formed in the reaction. Further, the latter method handles a high concentration of peroxides and is very dangerous especially in commercial production where large amounts of peroxides are used.

In connection with the latter method above described, it is believed that the oxidation of m-diisopropylbenzene produces resorcinol through hydroperoxides such as 1,3-di(2l-hydroperoxy-2-propyl)benzene, as is described in Japanese Patent Publication No. 58-52972. However, no such compound as has a hydroxyl group and a hydroxyl-containing alkyl group bonded at a m-position thereto has been utilized as a starting material for the production of resorcinol.

It is also known that the oxidation of benzene derivatives having one or more isopropyl groups in the molecule in the presence of a catalyst of an organocobalt complex produces organic hydroperoxides, as is described in Japanese Patent Laid-open No. 50-37741. However, this literature specifically discloses the production of p-isopropylhydroperoxyphenol using p-isopropylphenol as a starting material, but is silent about 3-(2-hydroperoxy-2-propyl)phenol, which is now provided according to the invention.

It is further known that 4-(2-hydroxy-2-propyl)phenol, a structural isomer of the 3-(2-hydroxy-2-propyl)phenol, is obtained by the oxidation of p-isopropylphenol with molecular oxygen in the presence of an organocobalt complex catalyst. However, the oxidation of m-isopropenylphenol in the presence of the same organocobalt complex catalyst fails to provide the objective 3-(2-hydroperoxy-2-propyl)phenol, but results in different products.

On the other hand, 3-hydroxyacetophenone has heretofore been produced by nitration of acetophenone, reduction, diazotization and then hydrolysis. However, the process uses large amounts of strong acids and metal salts, to produce large amounts of wastes including waste water, and also, as the case may be, toxic gases.

As above set out, there has been known no method of producing resorcinol or 3-hydroxyacetophenone in a safe and efficient manner.

The present inventors have made intensive investigations to establish a method of producing resorcinol safely and efficiently, and have found that a novel organic hydroperixide, 3-(2-hydroperoxy-2-propyl)phenol is readily obtained in high purity and in high yield by the oxidation of 3-(2-hydroxy-2-propyl)phenol or m-isopropenylphenol, and further that the acid-decomposition of the hydroperoxide provides resorcinol in high yield, thus having accomplished the invention.

It is, therefore, an object of the invention to provide a novel hydroperoxide, i.e., 3-(2-hydroperoxy-2-propyl)phenol.

It is a further object of the invention to provide a method of producing 3-(2-hydroperoxy-2-propyl)phenol.

It is still an object of the invention to provide a method of producing resorcinol using the hydroperoxide as a starting material.

In accordance with the invention, there is provided a novel hydroperoxide, 3-(2-hydroperoxy-2-propyl)phenol, which is represented by the structural formula below.

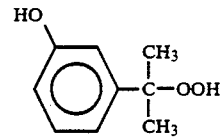

A first method of producing 3-(2-hydroperoxy-2-propyl)phenol comprises: oxidizing 3-(2-hydroxy-2-propyl)phenol with hydrogen peroxide in the presence of an acid catalyst.

The catalyst usable includes inorganic acids such as sulfuric acid, phosphoric acid, boric acid, hydrochloric acid, hydrosilicofluoric acid, tungstic acid, molybdic acid, and organic acids such as arenesulfonic acids, e.g., p-tuluenesulfonic acid, with sulfuric acid most preferred. The catalyst may be used alone or combined. The amount of the acid catalyst may vary depending upon the catalyst used, and for example, when sulfuric acid is used, it is used in such amount as is contained in the reaction mixture usually in amounts of about 10-10000 ppm.

The oxidation of 3-(2-hydroxy-2-propyl)phenol with hydrogen peroxide may be carried out in the absence of a solvent, but preferably in the presence of a solvent which is stable both to 3-(2-hydroxy-2-propyl)phenol and hydrogen peroxide. The solvent usable therefore may be exemplified by water, lower aliphatic carboxylic acid such as acetic acid or propionic acid, aliphatic or aromatic nitriles such as acetonitrile or benzonitrile. The solvent usable further includes, for example, phenol, ethyl acetate, chloroform, aliphatic or aromatic nitrated hydrocarbons such as nitromethane, nitroethane or nitrobenzene, sulfides or sulfoxides such as carbon disulfide or dimethylsulfoxide, lower aliphatic alcohols or polyhydric alcohols such as methanol, ethanol or glycerine, amides such as dimethylformamide, ethers such as tetrahydrofuran or 1,4-dioxane, aromatic hydrocarbons such as benzene, toluene, xylene, and aliphatic ketones such as acetone or methyl isobutyl ketone. These solvents may be used alone or as a mixture of two or more. However, among the above exemplified are in particular preferred acetone, 1,4-dioxane, acetonitrile or a mixture of these since both 3-(2-hydroxy-2-propyl)phenol and hydrogen peroxide are very soluble therein.

Any form of hydrogen peroxide may be used in the reaction, however, an aqueous solution of hydrogen peroxide which contains hydrogen peroxide in amounts of about 30-70% by weight is preferred from the standpoint of safety and reactivity. If necessary, sodium peroxide, potassium peroxide or calcium peroxide may be used in place of hydrogen peroxide, or as a mixture with hydrogen peroxide.

The hydrogen peroxide may be used in amounts of not less than about one mole in terms of active oxygen in relation to one mole of 3-(2-hydroxy-2-propyl)phenol used. More preferably, hydrogen peroxide is used in amounts of 1.1-3 moles as active oxygen in relation to one mole of 3-(2-hydroxy-2-propyl)phenol used from the standpoint of reaction efficiency and process economy.

The reaction may be carried out at temperatures of about $-30°$ to $120°$ C., preferably of about $10°-50°$ C., for a time usually of about 1-20 hours.

After the oxidation reaction, the catalyst is removed from the reaction mixture, and then the reaction mixture is extracted with a suitable organic solvent, for example, with ether or chloroform, and the recrystallization from, for example, chloroform, provides 3-(2-hydroperoxy-2-propyl)phenol in a high purity usually of not less than about 95%.

The novel hydroperoxide of the invention, 3-(2-hydroperoxy-2-propyl)phenol is colorless crystals, and has a melting point of $88°-89°$ C., and a decomposition point of $175°$ C. The hydroperoxide is useful as an intermediate for the production of resorcinol or m-hydroxyacetophenone, as will be described hereinafter, but also as a polymerization initiator, cross-linking agent or oxidant. In these applications, the hydroperoxide has a large temperature difference between the melting and decomposition points, so that it is advantageously used as a melt where necessary.

Furthermore, the hydroperoxide of the invention is stable in acidic conditions, as illustrated by the fact that it is produced in acidic conditions, contrary to unstability of many other hydroperoxides in general.

A second method of producing 3-(2-hydroperoxy-2-propyl)phenol is provided in accordance with the invention, which comprises: oxidizing m-isopropenylphenol with hydrogen peroxide in the presence of an acid catalyst.

The acid catalyst usable includes phosphoric acid, polyphosphoric acid, sulfuric acid, heteropolyacids such as phosphotungstic acid or phosphomolybdic acid, cation exchange resins, hydrogen boride and boron trifluoride-ether complexes, with phosphoric acid most preferred. The amount of the catalyst used may vary depending upon the catalyst used, however, it is in general in the range of about 0.1-10% by weight based on the reaction mixture.

Similarly to the first method, there is no limiting to form of hydrogen peroxide used in the second method, but about 30-70% by weight aqueous solutions are preferred from the standpoint of safety and reactivity. There is also no limiting in the amount of hydrogen peroxide used, but an amount of not less than an equivalent required in the oxidation of m-isopropenylphenol to 3-(2-hydroperoxy-2-propyl)phenol is preferred.

The oxidation of m-isopropenylphenol with hydrogen peroxide may also be carried out in the absence of a solvent, but preferably in the presence of a solvent which is stable in the reaction conditions. The solvent usable may be the same as described hereinbefore, and acetonitrile is most preferred.

The reaction may be carried out at temperatures in the range of about $0°-100°$ C., preferably in the range of about $20°-60°$ C. over a period usually of about 10-18 hours, and may be carried out usually under normal pressures, although if desired either under increased or reduced pressures. Further, the reaction may be effected either in batchwise or continuous manners.

After the reaction, the resultant hydroperoxide may be separated by conventional manners. By way of example, after the removal of the catalyst, the reaction mixture is extracted with a suitable organic solvent, such as ether or chloroform, and the recrystallization from, for example, chloroform, provides 3-(2-hydroperoxy-2-propyl)phenol in a high purity.

Among the two methods of the production of 3-(2-hydroperoxy-2-propyl)phenol as described, the second is more advantageous than the first since the starting material used therein, m-isopropenylphenol, is more readily and less expensively available than 3-(2-hydroxy-2-propyl)phenol.

However, according to the invention, 3-(2-hydroperoxy-2-propyl)phenol is readily obtained in a high yield in a pure form by either method since the 2-hydroxy-2-propyl group or isopropenyl group only is readily oxidized to a hydroperoxypropyl group with hydrogen peroxide, hence the oxidation reaction is of a high selectivity and is attended by the production of only small amounts of undesired byproducts. Moreover, the oxidation reaction can be effected under mild and readily controllable conditions.

In accordance with the invention, there is provided a method of producing resorcinol which comprises: decomposing the 3-(2-hydroperoxy-2-propyl)phenol in the presence of an acid catalyst. The catalyst used is the same as that used in the oxidation of 3-(2-hydroxy-2-propyl)phenol or isopropenylphenol with hydrogen peroxide, and includes, for example, inorganic acids such as sulfuric acid, phosphoric acid, hydrochloric acid, boric acid, hydrosilicofluoric acid, tungstic acid, molybdic acid, heteropolyacids such as phosphotungstic acid or phosphomolybdic acid, cation exchange resins, hydrogen boride and boron trifluoride-ether complexes, and organic acids such as arenesulfonic acids, e.g., p-toluenesulfonic acid, with sulfuric acid or phosphoric acid most preferred. These catalysts may be used alone or combined. The amount of the acid catalyst may vary depending upon the catalyst used. For example, when sulfuric acid is used, it is used in amounts of about 0.001-1% by weight based on the reaction mixture.

The decomposition of 3-(2-hydroperoxy-2-propyl)phenol may also be carried out in the absence of a solvent, but the use of a solvent is preferred. The solvent usable is the same as those used in the oxidation of 3-(2-hydroxy-2-propyl)phenol or m-isopropenylphenol which are described hereinbefore. However, benzene, toluene, acetone, methyl isobutyl ketone, acetonitrile, 1,4-dioxane or a mixture of two or more of these are in particular preferred in the decomposition reaction of the hydroperoxide.

The reaction temperature may be in the range of about $0°-150°$ C., preferably in the range of about $50°-100°$ C., and at temperatures higher than those where the oxidation of 3-(2-hydroxy-2-propyl)phenol is carried out. The reaction period may be usually from about 5 minutes to about one hour, although not critical.

After the completion of the reaction, an aqueous alkaline solution such as a sodium hydroxide solution is added to the reaction mixture to neutralize the acid catalyst in the reaction mixture, and then the solvent is removed from the reaction mixture, to provide resorcinol. The resorcinol may be purified by extraction or distillation under reduced pressures, if necessary.

As above set forth, resorcinol may be produced first by producing 3-(2-hydroperoxy-2-propyl)phenol by the oxidation of 3-(2-hydroxy-2-propyl)phenol or m-isopropenylphenol, separating and purifying the hydroperoxide, and then by the acid-decomposing the hydroperoxide, but it is of course possible to produce resorcinol by acid-decomposing the hydroperoxides as produced by the oxidation of 3-(2l-hydroxy-2-propyl)phenol or m-isopropenylphenol.

According to the invention, resorcinol is obtained in high purity and in high yield, and the reaction is accompanied by the production of undesired by-products only in small amounts since high purity 3-(2-hydroperoxy-2-propyl)phenol is obtained by the oxidation of 3-(2-hydroxy-2-propyl)phenol or m-isopropenylphenol according to the invention.

3-(2-Hydroperoxy-2-propyl)phenol of the invention is also useful as an intermediate for the production of m-hydroxyacetophenone. Namely, the reaction of 3-(2-hydroperoxy-2-propyl)phenol in the presence of a catalyst of iron or copper salts provides m-hydroxyacetophenone.

The invention will now be described with reference to examples, however, the examples are illustrative only, and are not to be construed as limiting to the invention.

EXAMPLE 1

Production of 3-(2-hydroperoxy-2-propyl)phenol

An amount of 1.1 g of a 60% by weight of aqueous hydrogen peroxide solution and 5 mg of concentrated sulfuric acid were added to a solution of 3-(2-hydroxy-2-propyl)phenol in 20 ml of acetonitrile, and the reaction was carried out at 25° C. over a period of 4.5 hours.

After the reaction, the reaction mixture was neutralized with an excess amount (1 g) of sodium hydrogen carbonate, filtered, and the filtrate was concentrated under reduced pressures. An amount of 50 ml of ether was added to the concentrate, and the resultant ether dispersion was added to water, thereby to retain the reaction products in the ether phase, while to transfer by-products into the water phase. The ether extract was concentrated by removing the ether by distillation under reduced pressures.

The resultant residual solid was then recrystallized from chloroform, to provide 1.2 g of colorless crystals in a purity of 98.4% (based on a DSC method) in an yield of 77%.

Figure 2:
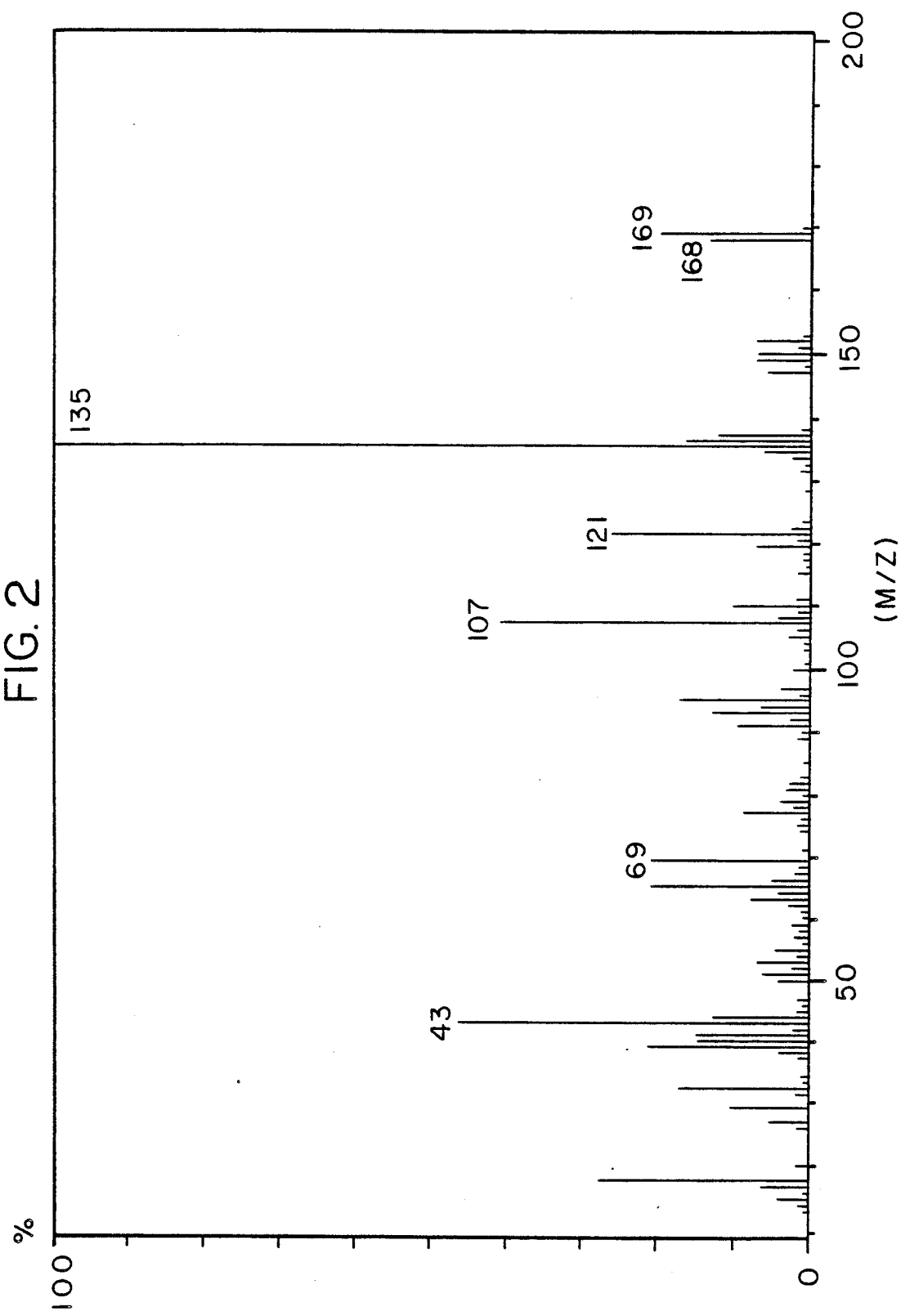
Figure 3:
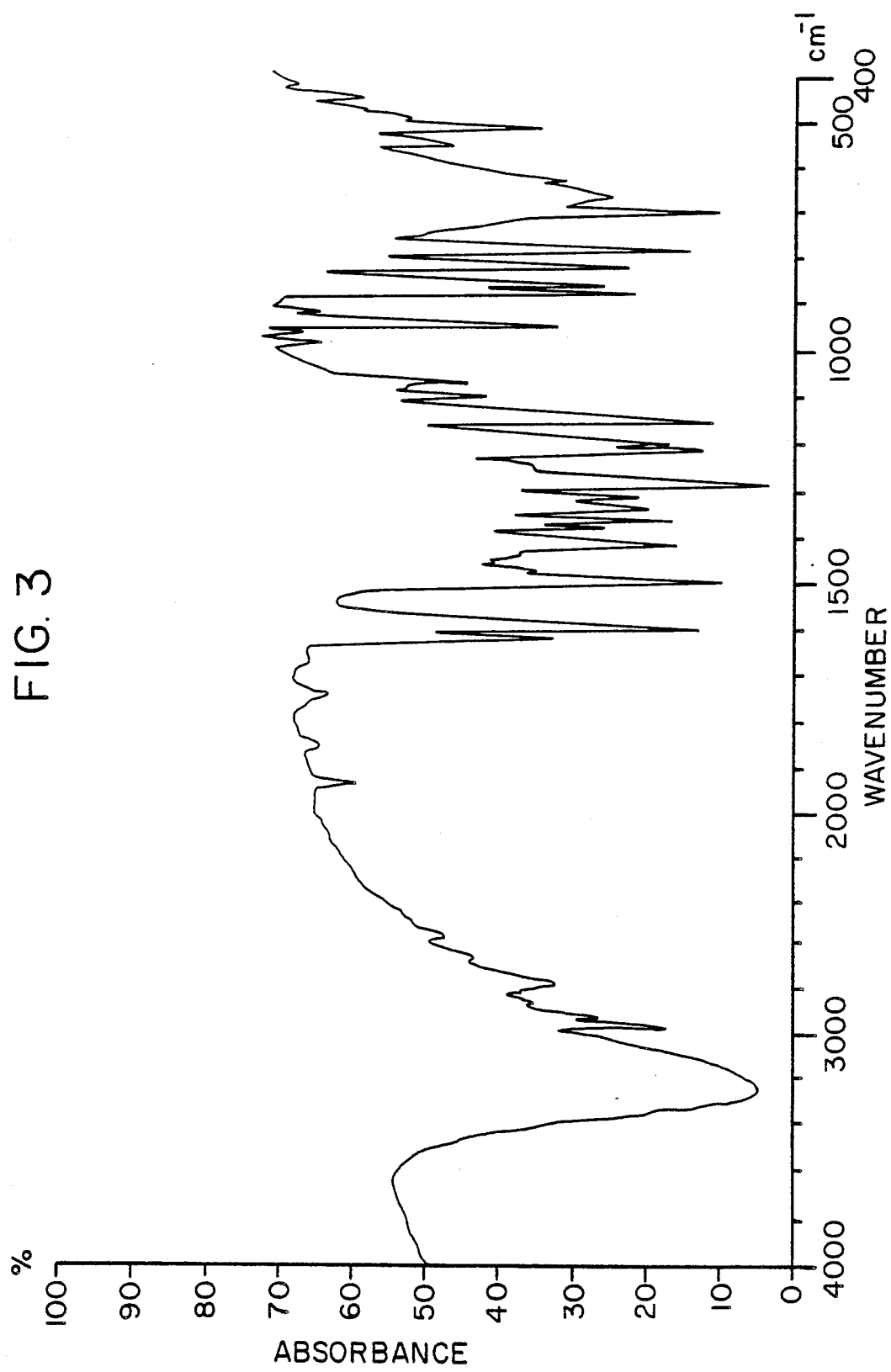

FIGS. 1, 2 and 3 are $^1$H-NMR, mass and IR spectra, respectively of 3-(2-hydroperoxy-2-propyl)phenol. Melting point: 88°–89° C.

| Elemental analysis as $C_9H_{12}O_3$: | | | |
|---|---|---|---|
| | C | H | O |
| Calculated: | 64.27 | 7.19 | 28.54 |
| Found: | 64.06 | 6.61 | 27.12 |

IR spectral data (KBr, cm$^{-1}$): 1620, 1590, 1280, 1150.

(Stability of 3-(2-hydroperoxy-2-propyl)phenol in an acid solution)

An amount of 0.5 g of 3-(2-hydroperoxy-2-propyl)phenol was dissolved in 10 ml of acetonitrile at room temperatures, and there was added thereto 0.5 g of an 1% aqueous sulfuric acid solution. After standing the resultant solution for one hour at room temperatures, the retention of the hydroperoxide in the solution was found 98% as measured by means of liquid chromatography.

On the contrary, substantially no 4-(2-hydroperoxy-2-propyl)phenol was found to retain in the same acidic conditions, and the hydroperoxide was found very unstable.

EXAMPLE 2

Production of resorcinol

An amount of 1.68 g of 3-(2-hydroperoxy-2-propyl)phenol was dissolved in 20 ml of toluene, and were added thereto 5 mg of concentrated sulfuric acid, followed by refluxing for 15 minutes under heating.

After the completion of the reaction, the reaction mixture was neutralized. The reaction mixture was found to contain resorcinol by liquid chromatographic analysis.

Sodium bisulfite was added to the reaction mixture to decompose the hydroperoxides in the reaction mixture, precipitates were removed by filtration, the solvent was removed by distillation under reduced pressures, and the residual was distilled, to provide 0.77 g of resorcinol in an yield of 70%.

EXAMPLE 3

Production of 3-(2-hydroperoxy-2-propyl)phenol

An amount of 2.8 g of a 60% by weight of aqueous hydrogen peroxide solution (50 mmol) and 0.2 g of sulfuric acid were added to a solution of 1.34 g (10 mmol) of m-isopropenylphenol in 20 ml of acetonitrile, and the reaction was carried out at 40° C. over a period of 30 minutes.

After the reaction, the reaction mixture was found to contain 0.5 g (3 mmol) of 3-(2-hydroperoxy-2-propyl)phenol by liquid chromatographic analysis.

EXAMPLE 4

Production of 3-(2-hydroperoxy-2-propyl)phenol

An amount of 2.8 g of a 60% by weight of aqueous hydrogen peroxide solution (50 mmol) and 1.25 g of phosphoric acid were added to a solution of 1.34 g (10 mmol) of m-isopropenylphenol in 20 ml of acetonitrile, and the reaction was carried out at 50° C. over a period of 24 hours.

After the reaction, the reaction mixture was found to contain 0.59 g (3.5 mmol) of 3-(2-hydroperoxy-2-propyl)phenol by liquid chromatographic analysis.

EXAMPLE 5

Production of 3-(2-hydroperoxy-2-propyl)phenol

An amount of 2.8 g of a 60% by weight of aqueous hydrogen peroxide solution (50 mmol) and 1.25 g of phosphoric acid were added to 13.4 g (100 mmol) of m-isopropenylphenol, and the reaction was carried out at 50° C. over a period of one hour.

After the reaction, the reaction mixture was found to contain 1.68 g (10 mmol) of 3-(2-hydroperoxy-2-propyl)phenol by liquid chromatographic analysis.

What is claimed is:

1. A method of producing 3-(2-hydroperoxy-2-propyl)phenol which comprises: oxidizing m-isopropenylphenol with hydrogen peroxide at a temperature of from about 0°–100° C. in at least one solvent selected from the group consisting of aliphatic nitriles, aromatic nitriles, aromatic hydrocarbons, acetone and 1,4-dioxane in the presence of an acid catalyst selected from the group consisting of phosphoric acid, polyphosphoric acid, sulfuric acid, heteropolyacids, cation exchange resins, hydrogen boride and boron trifluoride-ether complexes.

2. The method of producing 3-(2-hydroperoxy-2-propyl)phenol as claimed in claim 1 wherein the aliphatic nitrile is acetonitrile.

3. The method of producing 3-(2-hydroperoxy-2-propyl)phenol as claimed in claim 1 wherein the aromatic hydrocarbon is at least one of benzene, toluene and xylene.

4. The method of producing 3-(2-hydroperoxy-2-propyl)phenol as claimed in claim 1 wherein the acid catalyst is sulfuric acid or phosphoric acid.

* * * * *